(12) United States Patent
Nakano (10) Patent No.: US 8,354,636 B2
(45) Date of Patent: Jan. 15, 2013

(54) MASS SPECTROMETER

(75) Inventor: Tomohito Nakano, Nishikyo-ku (JP)

(73) Assignee: Shimadzu Corporation, Kyoto (JP)

( * ) Notice: Subject to any disclaimer, the term of this patent is extended or adjusted under 35 U.S.C. 154(b) by 244 days.

(21) Appl. No.: 13/020,750

(22) Filed: Feb. 3, 2011

(65) Prior Publication Data

US 2011/0204223 A1 Aug. 25, 2011

(30) Foreign Application Priority Data

Feb. 23, 2010 (JP) ................................ 2010-037783

(51) Int. Cl.
*B01D 59/44* (2006.01)
(52) U.S. Cl. ......................... 250/288; 250/281; 250/289
(58) Field of Classification Search ........................ None
See application file for complete search history.

(56) References Cited

U.S. PATENT DOCUMENTS

| | | | | |
|---|---|---|---|---|
| 5,753,910 | A * | 5/1998 | Gourley et al. | 250/288 |
| 6,653,624 | B2 | 11/2003 | Fukuda et al. | 250/288 |
| 6,809,312 | B1 * | 10/2004 | Park et al. | 250/281 |
| 2001/0050336 | A1 | 12/2001 | Fukuda et al. | 250/288 |
| 2008/0073188 | A1 * | 3/2008 | Emura et al. | 200/50.12 |
| 2008/0203737 | A1 * | 8/2008 | Tomaszewski et al. | 292/216 |

FOREIGN PATENT DOCUMENTS

| | | | |
|---|---|---|---|
| JP | 2001-343363 | | 12/2001 |
| JP | 2003013634 A | * | 1/2003 |
| JP | 2009294086 A | * | 12/2009 |

* cited by examiner

*Primary Examiner* — David A Vanore
*Assistant Examiner* — Andrew Smyth
(74) *Attorney, Agent, or Firm* — DLA Piper US LLP (57) ABSTRACT

Problem: To provide a mass spectrometer wherein the door can be easily opened even when the door becomes stuck to a third wall surface.

Solution: A mass spectrometer comprising a door 50 can be opened and closed and a lever 60 having a straight-shaped section 60*a* that is rotatable about a rotation shaft that is perpendicular to a first edge, wherein the rotation in a forward direction of one end of the straight-shaped section 60*a* of the lever 60 by a person taking measurements when the door 50 is closed causes a male part 61 formed on the lever 60 to interfere with and become locked with a female part 62 that is formed on an enclosure 110, thus making the door 50 unopenable and unclosable while the rotation in a reverse direction of the one end of the straight-shaped section 60*a* of the lever by a person taking measurements creates an unlocked state that allows the door 50 to be opened and closed and the other end of said straight-shaped section 60*a* of the lever 60 presses against a part of a third wall surface 110*c* that creates a force to open the door 50.

4 Claims, 9 Drawing Sheets

MASS SPECTROMETER

CROSS-REFERENCE TO THE RELATED APPLICATIONS

This application claims the benefit of priority under 35 USC 119 to Japanese Patent Application No. 2010-037783, filed on Feb. 23, 2010, the entire contents of which are incorporated herein by reference.

TECHNICAL FIELD

The present invention relates to a mass spectrometer that is equipped with an ionization chamber and relates in particular to a liquid chromatograph mass spectrometer that is equipped with an ionization chamber for ionizing liquid specimens that are discharged from a liquid chromatograph and a mass spectrometer to which ions are introduced from the ionization chamber.

BACKGROUND ART

A liquid chromatograph mass spectrometer (LC/MS) comprises a liquid chromatograph unit (LC unit) for separating liquid specimen into its components and discharging the liquid specimen according to its components, an ionization chamber (interface unit) for ionizing the specimen components that are discharged from the LC unit and a mass spectrometer (MS unit) for detecting ions that are introduced from the ionization chamber. Various ionization methods are used for the ionization of liquid specimen in an ionization chamber, but atmospheric pressure ionization such as atmospheric pressure chemical ionization (APCI) and electrospray ionization (ESI) are often used.

Specifically, with atmospheric pressure chemical ionization, the tip of a nozzle that is connected to the end of a column of an LC unit is disposed in a direction pointing towards the interior of the ionization chamber, and a probe electrode is disposed in front of the nozzle tip. Droplets of the specimen that are atomized by heating at the nozzle are ionized by chemical reaction with carrier gas ions (buffer ions) that are generated by corona discharge from the probe electrode. With electrospray ionization, the tip of a nozzle that is connected to the end of a column of an LC unit is disposed in a direction pointing towards the interior of an ionization chamber, and a high voltage of approximately several kV is applied to the nozzle tip to generate a strong unequal electrical field. The electrical field causes the liquid specimen to separate according to its charge due to Coulomb attraction and atomize. When the specimen droplets come into contact with ambient air, the solvent in the specimen droplets evaporates, and gas ions are generated.

With atmospheric pressure chemical ionization and electrospray ionization, liquid specimens are ionized at near atmospheric pressure while the ionization chamber is kept at a high pressure (i.e., close to atmospheric pressure) and the mass spectrometer unit is kept at a low pressure (i.e., a high degree of vacuum). To maintain a pressure differential between the ionization chamber and the mass spectrometer unit, intermediate chambers and the like are disposed between the ionization chamber and the mass spectrometer unit with the degree of vacuum of the intermediate chambers being gradually increased. (See for example Patent Literature 1.)

Figure 5:
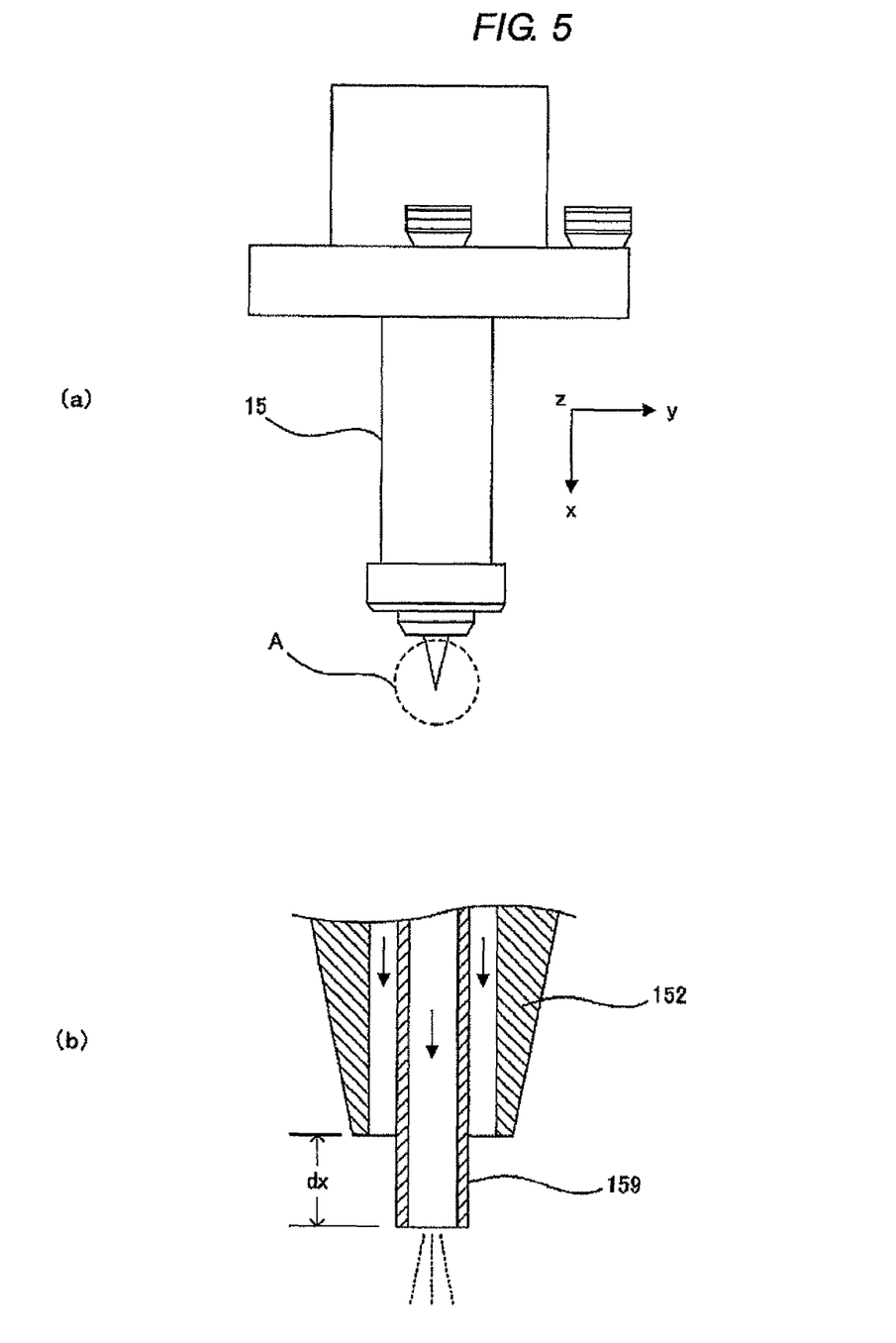
FIG. 5 shows a detailed view of the spray unit.
Figure 6:
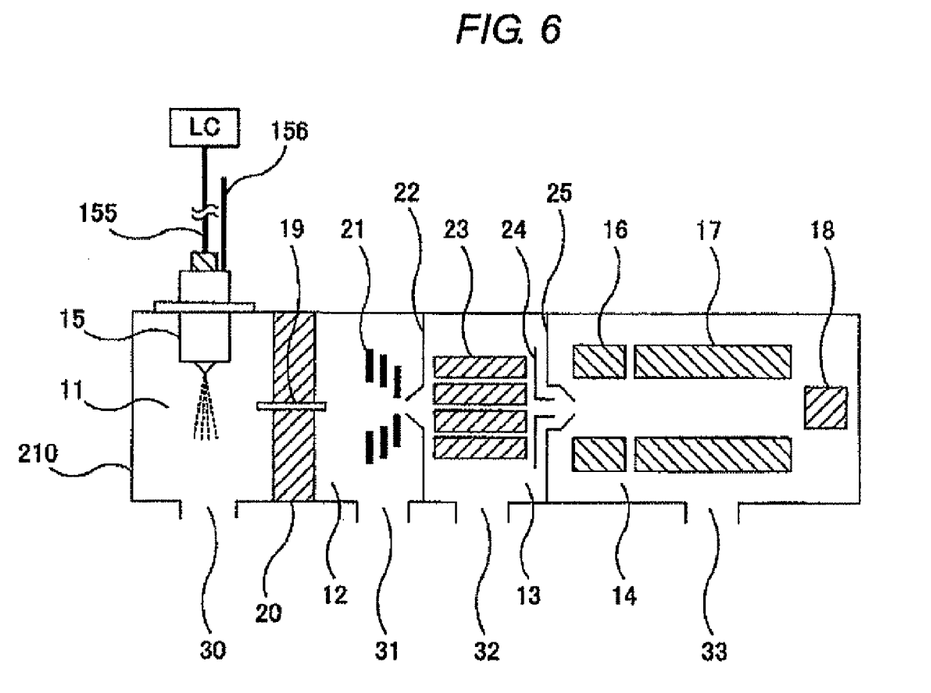
FIG. 6 shows a schematic view of the configuration of one example of a previous liquid chromatograph mass spectrometer that uses electrospray ionization.
Figure 7:
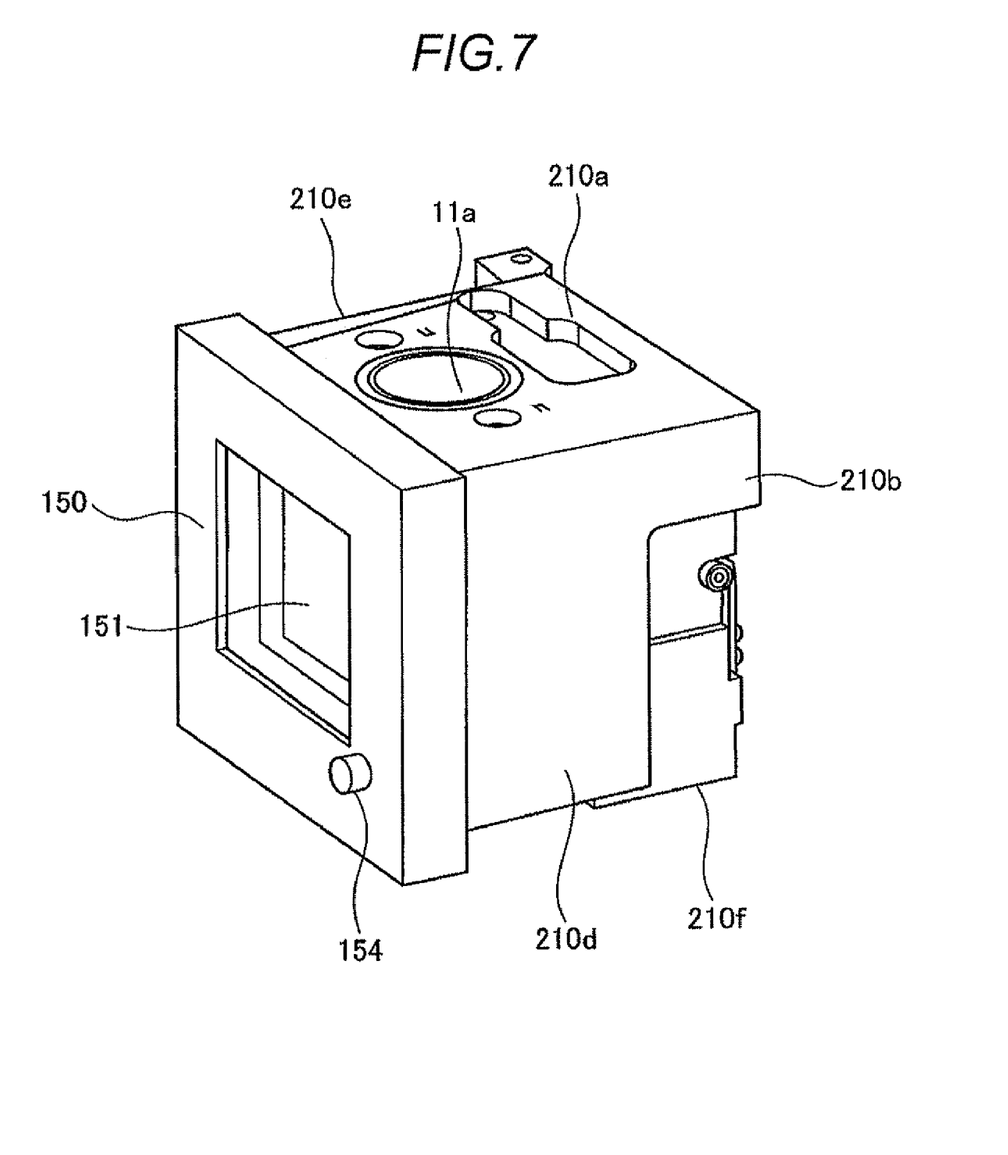
FIG. 7 shows perspective view of the ionization chamber shown in FIG. 6.
Figure 8:
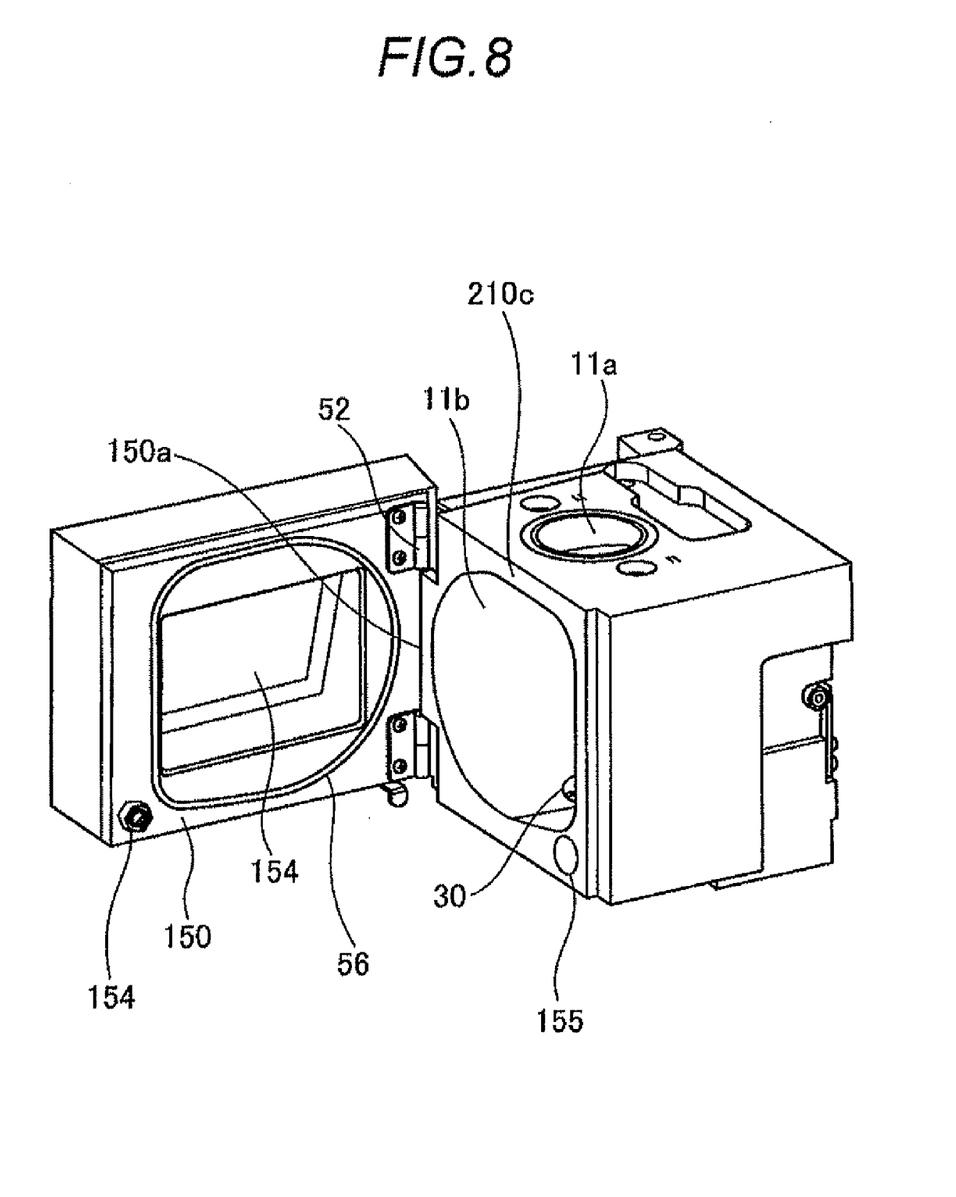
FIG. 8 shows perspective view of the ionization chamber shown in FIG. 6.

FIG. 6 shows a schematic view of the configuration of one example of a liquid chromatograph mass spectrometer that uses electrospray ionization. FIG. 7 and FIG. 8 show perspective views of the ionization chamber shown in FIG. 6. FIG. 5 shows a detailed view of the spray unit. FIG. 7 shows the ionization chamber with its door closed. FIG. 8 shows the ionization chamber with its door opened.

The liquid chromatograph mass spectrometer includes an ionization chamber 11 comprising a chamber (enclosure) 210, a first intermediate chamber 12 located adjacent to the ionization chamber 11, a second intermediate chamber 13 located adjacent to the first intermediate chamber 12 and a mass spectrometry chamber (MS unit) 14 located adjacent to the second intermediate chamber 13. These chambers are formed in succession and are each separated by a partition wall.

The liquid specimen that is separated into its components by the liquid chromatograph unit is supplied to the ionization chamber via flow path 155. Nebulized gas (nitrogen gas) is provided through flow path 156. The liquid specimen and the nebulized gas are supplied to spray (probe) 15 from where they are sprayed.

FIG. 5(a) shows a side view of the spray unit. FIG. 5(b) shows an enlarged sectional view of part A shown in FIG. 5. The spray unit 15 has a double-walled tubular structure. The liquid specimen that is supplied through flow path 155 is discharged from the inner side of the tube 159. The nitrogen gas that is supplied through flow path 156 is discharged through the space between the tube 159 and nozzle 152 that has a tubular shape. This arrangement results in the discharged liquid specimen to collide with nebulized gas that is discharged around the tube 159 and to atomize as it is sprayed.

Furthermore, a voltage source (not illustrated) is wired (not illustrated) to apply a high voltage of several kV to the tip of nozzle 152 to cause ionization.

In FIG. 5 through FIG. 8, spray unit 15 is used for electrospray ionization. The spray unit 15 is usually removably attached to the chamber 210. If the use of atmospheric pressure chemical ionization is desired, the spray unit 15 is removed and replaced on the chamber 210 by a unit with an integrated probe electrode for discharging purposes.

A position adjustment knob (not illustrated) is provided so that the tip of the spray unit 15 can engage in a substantially parallel movement over a predetermined range on a y-z plane that is orthogonal to the x-axis. After the position is suitably adjusted, the position of the tip of the spray unit is fixed using a position fixing knob. The spray unit 15 can also be pushed in and pulled out of the spray unit itself in the x-axis direction (so that the amount of protrusion dx can be adjusted). After the position is suitably adjusted, a nut (not illustrated) is used to fix the position.

The ionization chamber 11 includes a chamber 210 in the shape of a rectangular solid measuring 13 cm×13 cm×12 cm. The chamber 210 comprises a first wall surface (upper surface) 210a, a second wall surface (partition wall) 210b, a third wall surface (front surface) 210c, a fourth wall surface (right side surface) 210d, a fifth wall surface (left side surface) 210e and a sixth wall surface (lower surface) 210f. The internal space of the ionization chamber 11 is thus formed and enclosed by the upper surface 210a, partition wall 210b, front surface 210c, right side surface 210d, left side surface 210e and the lower surface 210f.

A circular opening 11a is formed in the upper surface 210a to provide a connection in the vertical direction. The spray unit 15 is installed in the opening 11a from above.

The partition wall 210b is provided to form a partition between the interior of the ionization chamber 11 and the interior of the first intermediate chamber 12. A heater block 20 with a temperature adjustment mechanism (not illustrated) incorporated therein is secured to the partition wall 210b. A solvent removal tube 19 having a tubular shape (outer diameter of 1.6 mm and inner diameter of 0.5 mm) is formed in the heater block 20 so that the interior of the ionization chamber 11 and the interior of the first intermediate chamber 12 are connected by the solvent removal tube 19. As fine droplets of the specimen and ions that are sprayed by the spray unit 15 pass through the solvent removal tube 19, the heating and collision provide the effect and function of promoting ionization and removing the solvent.

The inlet to the solvent removal tube 19 is oriented in a direction substantially perpendicular to the specimen spraying direction of the spray unit 15 so that large droplets of the specimen that are sprayed do not directly enter the solvent removal tube 19. A drain 30 is formed on the lower surface 210I in front of the specimen spraying direction of the spray unit 15 so that unnecessary specimen is discharged out through the drain 30.

A first ion lens 21 is disposed in the first intermediate chamber 12. An exhaust opening 31 which uses an oil rotary pump (RP) to create a vacuum for exhausting purpose is disposed on the lower surface of the first intermediate chamber 12. A skimmer 22 having an orifice is formed in the partition wall between the first intermediate chamber 12 and the second intermediate chamber 13. The orifice connects the interior of the first intermediate chamber 12 and the interior of the second intermediate chamber 13.

An octupole 23 and a focal lens 24 are disposed in the second intermediate chamber 13. An exhaust opening 23 through which exhausting is performed by a vacuum created by a turbo molecular pump (TMP) is disposed on the lower surface of the second intermediate chamber 13. An incoming lens 25 having an orifice is disposed in the partition wall between the second intermediate chamber 13 and the mass spectrometry chamber 14. The interior of the second intermediate chamber 13 and the interior of the mass spectrometry chamber 14 are connected by the orifice.

A first quadrupole 16, second quadrupole 17 and detector 18 are disposed in the mass spectrometry chamber 14. An exhaust opening 33 through which exhausting is performed by a vacuum created by a turbo molecular pump (TMP) is disposed on the lower surface of the mass spectrometry chamber 14.

The ion lens 21, octupole 23, focal lens 24 and the incoming lens 25 are each at some level of vacuum and provide a converging effect for efficiently sending to the next stage the ions that pass through them at particular speeds.

In a liquid chromatograph mass spectrometer such as the afore-described, the ions that are generated in the ionization chamber 11 are sent to the mass spectrometry chamber 14 via the solvent removal tube 19, first ion lens 21 in the first intermediate chamber 12, skimmer 22, octupole 23 and focal lens 24 in the second intermediate chamber 13 and incoming lens 25. After unnecessary ions are discharged by quadrupoles 16 and 17, only specific ions which reach detector 18 are detected.

The ion generation efficiency of ionization chamber 11 when using electrospray ionization can be increased by appropriately adjusting the positional relationship between the spray unit 15 which sprays the liquid specimen and the inlet of the solvent removal tube 19, by ensuring that the spray unit 15 is providing a normal spray, and by checking to keep the spray unit 15 clean. Performing such adjustments or check is facilitated if the interior of the ionization chamber 11 can be observed from the outside and the interior of the ionization chamber 11 opened. For this reason, with the liquid chromatograph mass spectrometer, a substantially square-shaped opening 11b (11 cm×11 cm) and a rectangular flat door 150 (18 cm×15 cm×2.5 cm) for covering opening 11b are formed on the front surface 210e. A rectangular observation window 151 (11 cm×8 cm) made of glass and the like is formed in the center of the door 150.

The door 150 opens and closes on hinges 52 pivoting about a first edge (left edge) 150a of a rectangular door. This allows a person performing the measurements to freely open and close the door 150 leading to the interior of the ionization chamber 11. So that the door 150 securely closes the opening 11b during measurements, an opening is formed at the lower right area of the door 150 where a screw can be inserted in the fore-to-aft direction. A person performing measurements inserts a male screw 154 from the front into the screw opening so as to engage with a screw hole 155 that is formed in the lower right area of the front surface 210c. This disables the door 150 from being opened or closed.

The door 150 has a laminated construction featuring a heat-resistant metallic cover, a metallic main body and a rubber O-ring 56 which are layered in this sequence starting from the front side.

PRIOR ART LITERATURE

Patent Literature

Patent Literature 1: JP 2001-343363 A

OVERVIEW OF THE INVENTION

Problems to be Solved by the Invention

However, with the afore-described liquid chromatograph mass spectrometer, the door 150 sometimes could not be easily opened after a measurement. To explain, because specimens are sprayed inside the ionization chamber 11, the front surface 210c and the O-ring 56 can stick together, at times to a degree that someone forcibly opening the door could get injured.

Means for Solving the Problems

To solve the above problem, the inventors studied for ways in which the door could be easily opened even when it was stuck. The use of male screws to make it impossible to open or close the door was not adopted since tightening and loosening a screw was inefficient as a method for securely closing the door. Instead of using male screws, a lever having a straight-shaped section was formed on a side surface of a second edge of the door that opposed a first edge of the door. The lever was made rotatable about a rotational axis extending perpendicularly to the first edge. With the door closed, by rotating one end of the straight-shaped section of the lever in a forward direction, a male part (cam) engages with a female part (pin) that is formed on the enclosure and locks the door, thus making the door impossible to be opened or closed. On the other hand, by rotating one end of the straight-shaped section of the lever in a reverse direction, the male part (cam) that is formed on the lever disengages from the female part (pin) that is formed on the enclosure, thus unlocking the door and allowing it to be opened and closed. In other words, the door is made openable and closable or unopenable and unclosable simply by rotating one end of the straight-shaped section of the lever. Furthermore, when the door is unlocked by rotating the straight-shaped section of the lever in the reverse direction, the other end of the straight-shaped section of the lever presses against a portion a surface of a third wall surface, creating a force that allows the door to be easily opened even if the door were to be stuck to the surface of the third wall.

To further explain, a mass spectrometer according to the present invention includes an ionization chamber for ionizing a specimen and a mass spectrometer to which ions are introduced from the ionization chamber. The ionization chamber includes an enclosure having a first wall surface, a second wall surface and a third wall surface and forming an internal space. A probe for spraying a specimen placed in the ionization chamber is installed on the first wall surface. A tube that connects the ionization chamber and the inside of a mass spectrometer is formed on the second wall surface. An opening that opens the inside of the ionization chamber is formed on the third wall surface. A rectangular flat door is provided for covering the opening. The door is openable and closable by rotating about a first edge of the rectangular door. A lever having a straight-shaped section was formed on the side surface of a second edge of the door that opposed a first edge of the door. The lever was made to be rotatable about a rotational axis that is perpendicular to the first edge. One end of the straight-shaped section of the lever is operated by a person taking the measurements. With the door closed, by rotating the one end of the straight-shaped section of the lever in a forward direction, a male part that is formed on the lever engages with a female part that is formed on the enclosure and locks the door, thus making the door unopenable and unclosable. On the other hand, by rotating the one end of the straight-shaped section of the lever in a reverse direction, the male part that is formed on the lever disengages from the female part that is formed on the enclosure, thus unlocking the door and allowing it to be opened and closed by the person taking the measurements. When the door is unlocked by rotating the straight-shaped section of the lever in the reverse direction, the other end of the straight-shaped section of the lever presses against a portion of a third wall surface, creating a force that opens the door.

Effects of the Invention

As afore-described, with the mass spectrometer according to the present invention, even if the door were to become stuck to the third wall surface, the door can be easily opened because the other end of the straight-shaped section of the lever presses against a part of the third wall surface. The person taking the measurements can make the door openable and closeable or unopenable and unclosable simply by rotating the one end of the straight-shaped section of the lever.

Means for Solving Other Problems and Their Effects

With the mass spectrometer according to the present invention, the distance from the one end of the lever to the rotational axis may be longer than the distance from the other end to the rotational axis. Doing so allows the door to be even more easily opened because of leverage.

Furthermore, with the mass spectrometer according to the present invention, the male part is a columnar structure that is formed on the lever, and the female part is a columnar structure that is formed on the enclosure. The first edge of the rectangular door is oriented to be extending vertically. The door is opened when it is pulled towards the person taking the measurements. When the door is locked, the male part with the columnar structure is positioned to the rear of the columnar structure of the female part but at the same height as the columnar structure of the female part. On the other hand, when the door is unlocked, the male part with the columnar structure need not necessarily be positioned at the same height as the columnar structure of the female part.

Furthermore, the mass spectrometer according to the present invention may include a cover that covers the door and the lever from the foreground. The cover may be fixed to the door and to the one end of the straight-shaped section of the lever so that the cover is rotatable about a rotational axis that is perpendicular to the first edge of the door. The cover is therefore rotatable about a rotational axis that is perpendicular to the first edge of the door while covering the door and the lever.

With the mass spectrometer according to the present invention, the cover hides the lever when viewed from the front, improving the appearance.

EMBODIMENTS OF THE INVENTION

An embodiment of the present invention is described next with reference to figures. However, the present invention is not limited to the embodiment described herein below, and needless to say, variations are possible without deviating from the gist of the present invention.

Figure 1:
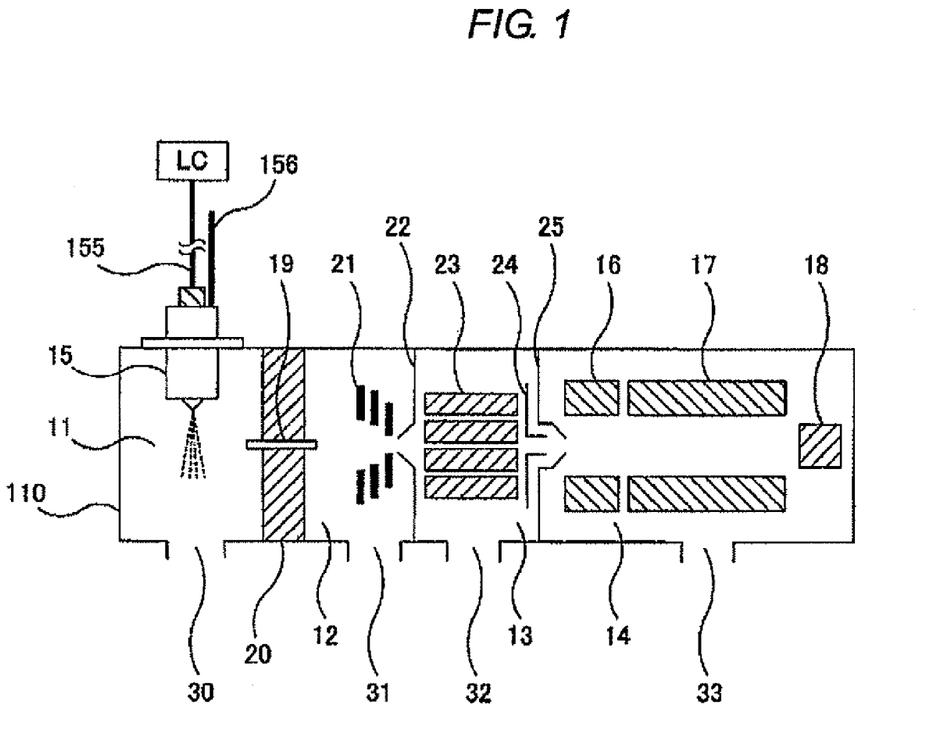
FIG. 1 shows a schematic view of the configuration of one example of a liquid chromatograph mass spectrometer according to the present invention that uses electrospray ionization.
Figure 2:
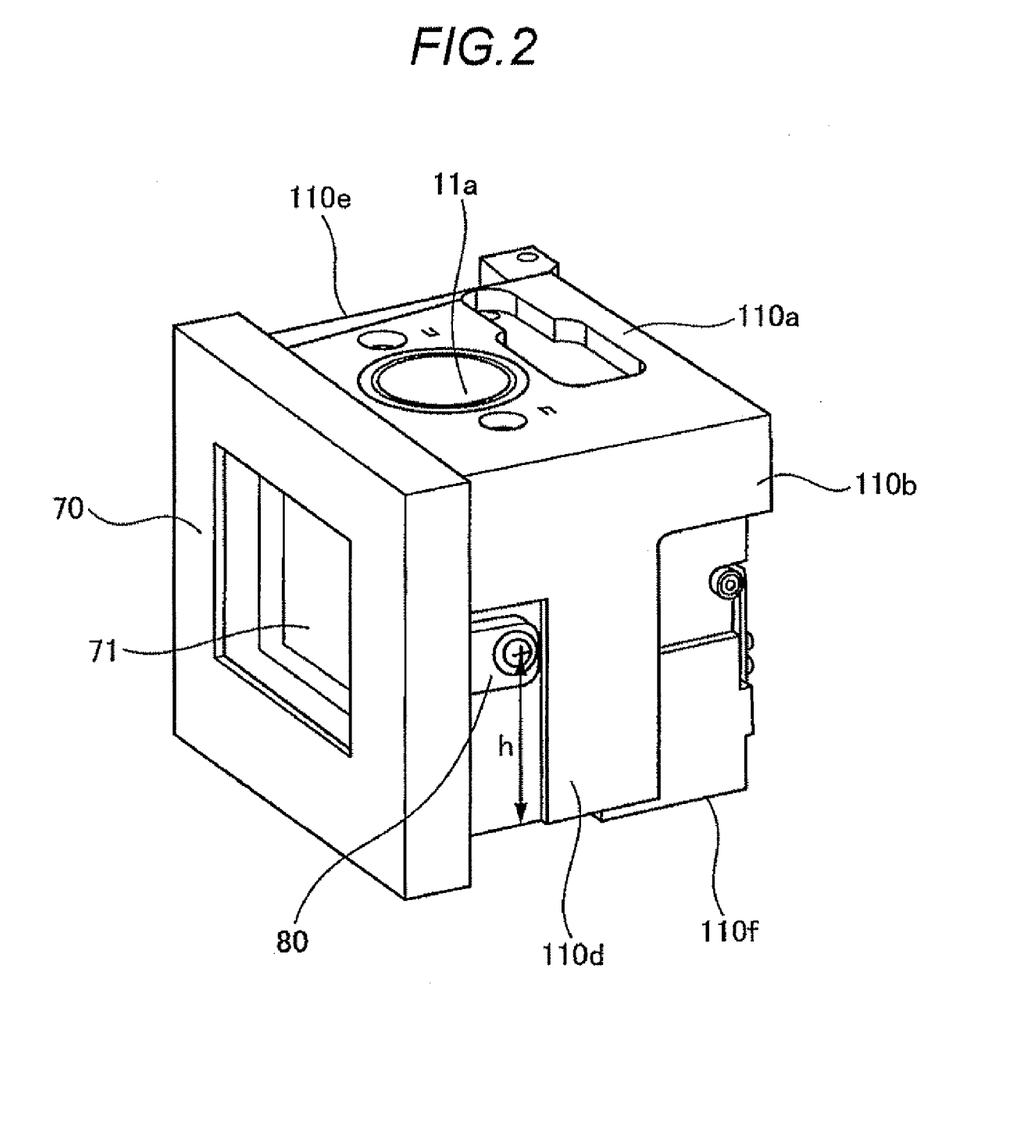
FIG. 2 shows a perspective view of the ionization chamber shown in FIG. 1.
Figure 3:
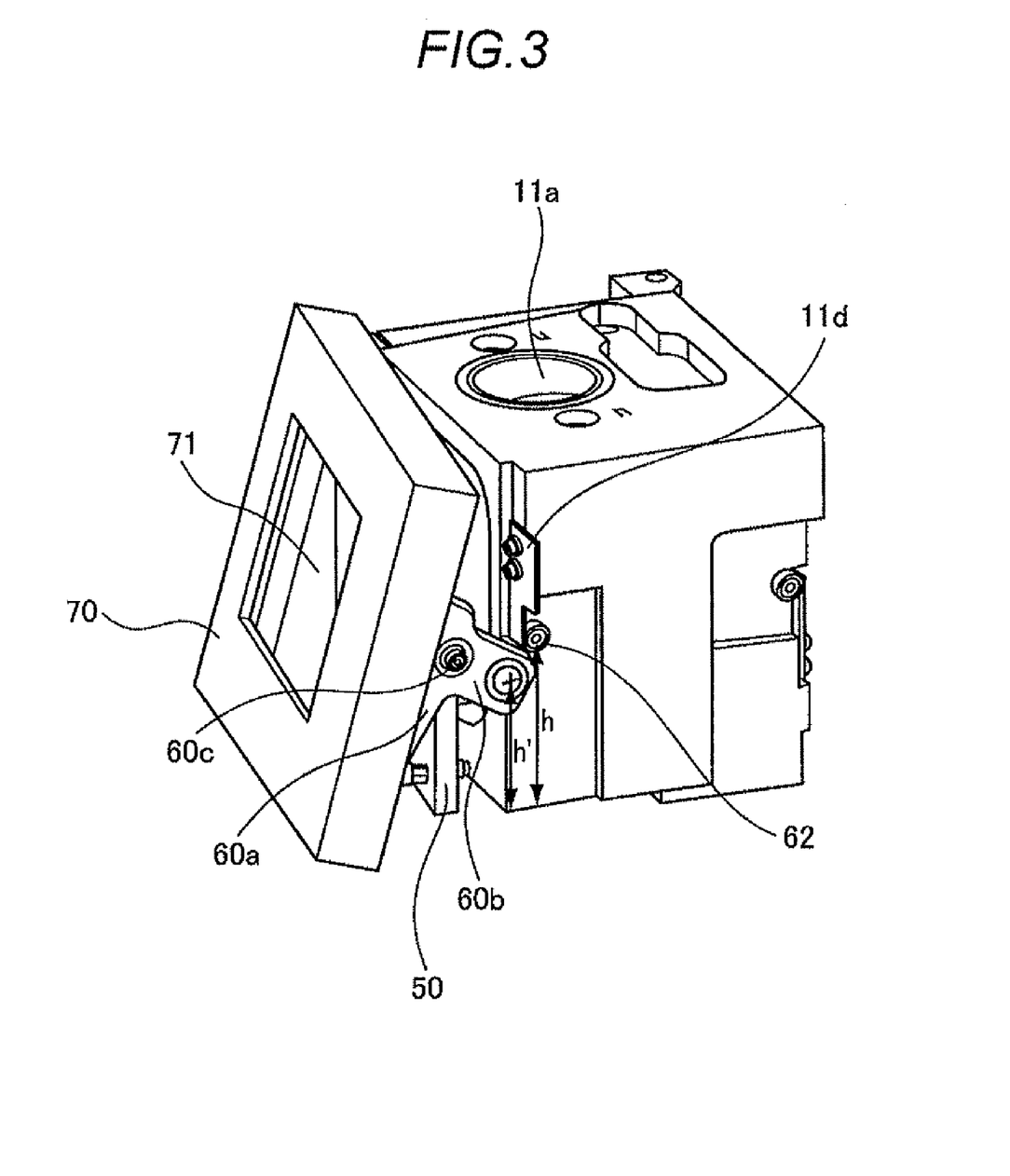
FIG. 3 shows a perspective view of the ionization chamber shown in FIG. 1.
Figure 4:
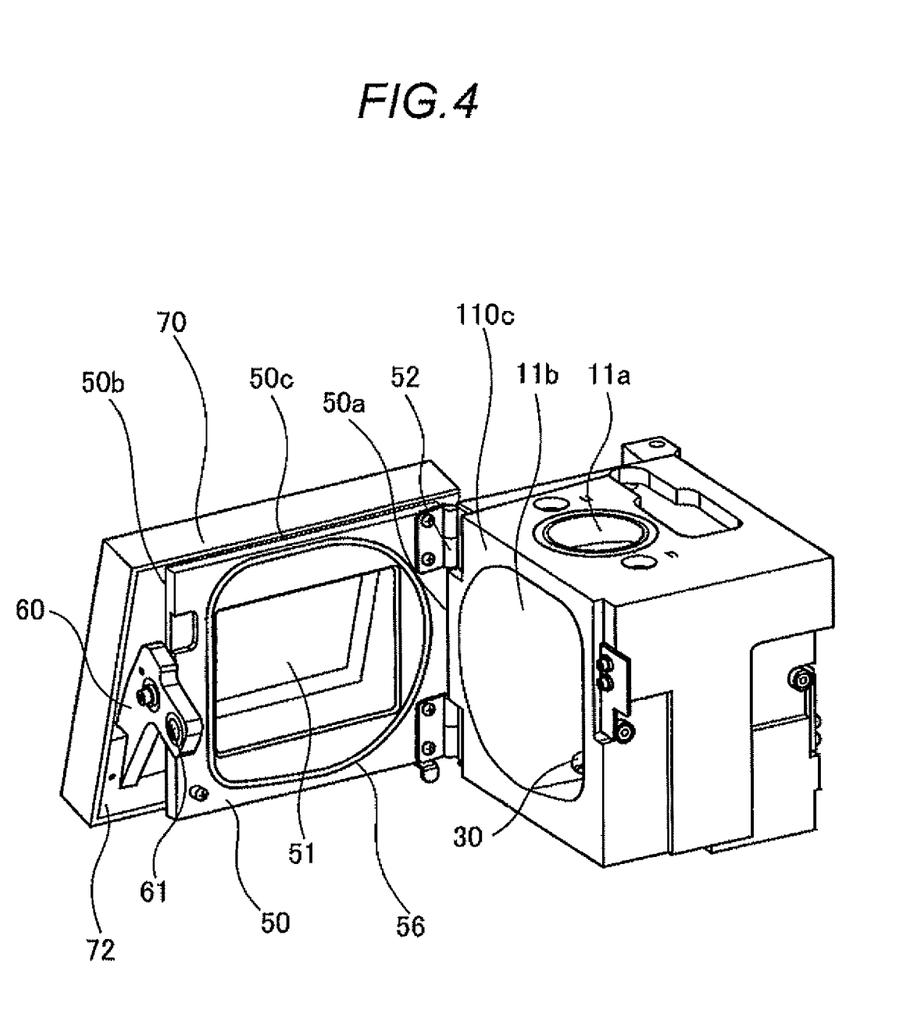
FIG. 4 shows perspective view of the ionization chamber shown in FIG. 1.

FIG. 1 shows a schematic view of the configuration of one example of a liquid chromatograph mass spectrometer according to the present invention that uses electrospray ionization. FIG. 2 through FIG. 4 show perspective views of the ionization chamber shown in FIG. 1. FIG. 2 shows the ionization chamber with the door closed. FIG. 3 shows the ionization chamber with the door opened. FIG. 4 shows the ionization chamber with the door opened. The same reference numbers are used for the same parts as in the figures for the previous liquid chromatograph mass spectrometer.

The liquid chromatograph mass spectrometer includes an ionization chamber 11 equipped with a chamber (enclosure) 110, a first intermediate chamber 12 located next to the ionization chamber 11, a second intermediate chamber 13 located next to the first intermediate chamber 12, and a mass spectrometry chamber (MS unit) 14 located next to the second intermediate chamber 13. These chambers are separated by partition walls and are formed in succession to each other.

The ionization chamber 11 includes a chamber 110 that is in the shape of a 13 cm×13 cm×12 cm rectangular solid. The chamber 110 includes a first wall surface (upper surface) 110a, a second wall surface (partition wall) 110b, a third wall surface (front surface) 110e, a fourth wall surface (right side surface) 110d, a fifth wall surface (left side surface) 110e and a sixth wall surface (lower surface) 110f. The internal space of the ionization chamber 11 is surrounded and formed by the upper surface 110a, partition wall 110b, front surface 110c, right side surface 110d, left side surface 110e and lower surface 110f.

Formed on the upper surface 110a is an opening 11a that opens vertically so that a spray unit 15 can be installed from above.

A partition wall 110b is provided as a partition between the interior of the ionization chamber 11 and the interior of the first intermediate chamber 12. A heater block 20 incorporating a temperature adjustment mechanism (not illustrated) is secured to the partition wall 110b. A solvent removal tube 19 with a tubular shape (outer diameter of 1.6 mm and inner diameter of 0.5 mm) is formed in the heater block 20. The interior of the ionization chamber 11 and the interior of the first intermediate chamber 12 are connected by the solvent removal tube 19.

The inlet to the solvent removal tube 19 is oriented to be substantially perpendicular to the specimen spraying direction of the spray unit 15 to prevent large droplets of the specimen that is sprayed from entering the solvent removal tube 19. A drain 30 is formed in the lower surface 110f that is located in front of the specimen spray direction by the spray unit 15 so that unneeded specimen is discharged through the drain 30.

A substantially square-shaped opening (11 cm×11 cm) is formed in the front surface 110c. A rectangular flat door 50 (18 cm×15 cm×2.5 cm) is formed to cover the opening 11b. An observation window 51 made of glass and the like is formed in the center of the door 50 which can be opened and closed by rotating about a first edge (left edge) 50a of the rectangular door by means of hinges 52.

The door 50 is constructed with a main part made of a metal and a rubber O-ring 56 laminated on the rear-facing surface of the main part.

A substantially T-shaped lever 60 is installed on the side surface of a second edge (right edge) 50b of door 50, the T-shaped lever having a straight-shaped section 60a and an extension 60b that extends a predetermined length (3 cm) from the straight-shaped section 60a.

Formed near the center of the straight-shaped section 60a is a rotational axis part 60c that allows rotation about an axis extending perpendicularly to the first edge 50a. The distance (7 cm) from one end of the straight-shaped section 60a of the lever 60 to the rotational axis part 60c is greater than the distance (2 cm) from the other end of the straight-shaped section 60a to the rotational axis part 60c. The lever 60 is installed so that one end of the straight-shaped section 60a is positioned at the bottom, the other end of the straight-shaped section 60a is positioned at the top, and the extension 60b is positioned at the rear.

A person taking measurements operates the one end of the straight-shaped section 60a of lever 60 and rotates the lever 60 in the forward direction and the reverse direction.

Formed on the left side surface of the extension 60b of lever 60 is a cam (male part) 61 of a cylinder (diameter of 1 cm and height of 0.6 cm) whose center axis is parallel to the rotational axis.

When the door 50 is closed, the extension 60b of the lever 60 is positioned to the right of the front surface 110c, and the straight-shaped section 60a of the lever 60 is positioned to the fore of the front surface 110c (top right extension plate 11d). In this condition, the straight-shaped section 60a of the lever 60 extends vertically in a straight line and becomes parallel to the front surface 110c (top right extension plate 11d).

The door 50 is opened by pulling on the one end of the straight-shaped section 60a of the lever 60. This causes the straight-shaped section 60a of the lever 60 to tilt with respect to the vertical direction, and the one end of the straight-shaped section 60a of the lever 60 to move away from the front surface 110c. However, since the other end of the straight-shaped section 60a of the lever 60 strikes against the top right extension plate 11d of the front surface 110c, a force tending to open the door 50 is applied. When the one end of the straight-shaped section 60a of the lever 60 is rotated so that it moves away from the front surface 110e, the other end of the straight-shaped section 60a of the lever 60 presses against the top right extension plate 11d of the front surface 110c, causing the door 50 to open. The distance (7 cm) from the one end of the straight-shaped section 60a of the lever 60 to the rotational axis part 60e is greater than the distance (2 cm) from the other end of the straight-shaped section 60a of the lever 60 to the rotational axis part 60c. The leverage that is created allows the door 50 to be easily opened.

A pin (female part) 62 of a cylinder (diameter of 1 cm and height of 0.6 cm) whose central axis is parallel to the rotation axis having a central is formed on the right side of the front surface 110c at a position of height h.

This arrangement means that, when the door 50 is closed, the cam 61 is positioned at the same height h as pin 62 but to the rear of pin 62 (locked state). Since cam 61 and pin 62 are at the same height, the door 50 cannot be opened or closed by rotating about the first edge 50a.

When the door 50 is opened, the person taking the measurements rotates the one end of the straight-shaped section 60a of the lever 60 so that the cam 61 rotates around its rotational axis and to the rear of the pin 62 so as to position itself at position h' which is lower than the height of the pin 62 (unlocked state). Because the cam 61 and the pin 62 are not at the same height, the door 50 can be opened and closed about the first edge 50a.

Figure 9A:
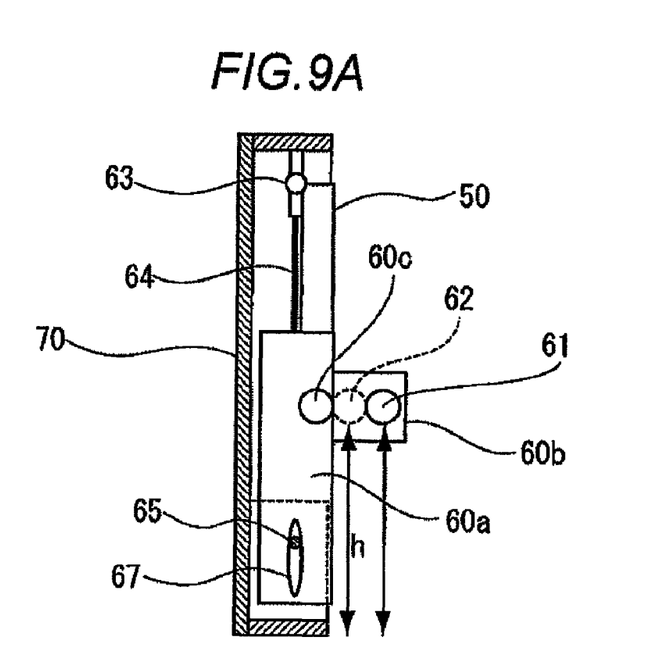
FIG. 9 shows a sectional view of the door and cover shown in FIG. 1.
Figure 9B:
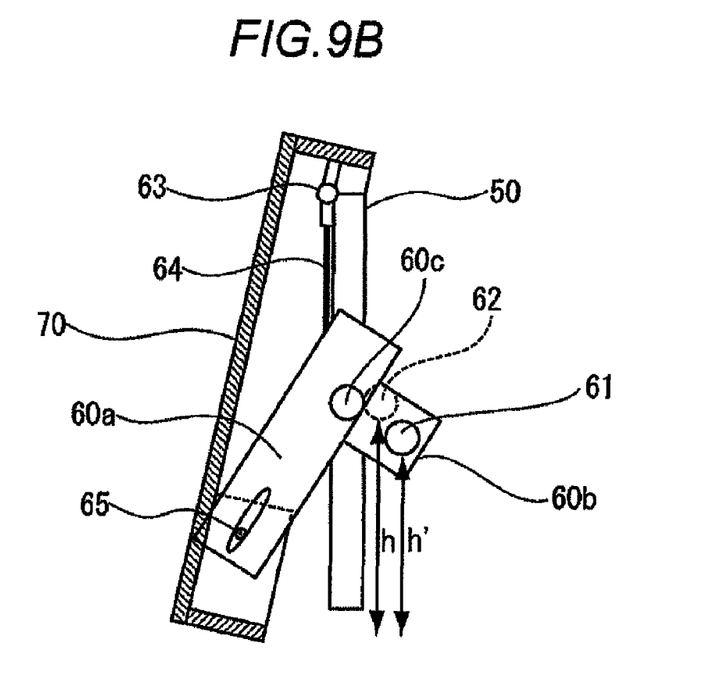

Furthermore, a heat-resistant cover 70 consisting of a square shell (18 cm×15 cm) with extending side surfaces is installed so as to cover the door 50 and lever 60 from the front. A rectangular observation window 71 (11 cm×8 cm) made of glass and the like is formed at the center of the side surface of the cover 70. FIG. 9 shows a sectional view of the door and the cover. FIG. 9(a) shows the door and the cover in the locked state. FIG. 9(b) shows the door and the cover in the unlocked state.

The top edge of the side surface of cover 70 is fixed to the top edge 50c of the door 50 by hinge 63 so that the top edge of the side surface is rotatable about a rotational axis that is perpendicular to the first edge 50a. A block 72 having a pin 65 is formed at the lower right portion of the side surface of cover 70 and is secured there by pin 65 which is inserted into an oval hole 66 that is formed at the one end of the straight-shaped section 60a of the lever 60. This allows the cover 70 to rotate together with the lever 60 about the top edge 50c of the door 50 while covering the door 50 and lever 60. When the door 50 is opened, a spring 64 prevents the side surface of cover 70 from becoming parallel with the door 50. When the door 50 is closed and locked, the side surface of the cover 70 becomes parallel to the door 50. When a person taking measurements closes the door 50 and pushes the cover 70 rearward, the door 50 becomes locked.

As afore-described, with the liquid chromatograph mass spectrometer according to the present invention, even if the front surface 110c and the door 50 were to get stuck together, the other end of the straight-shaped section 60a of the lever 60 presses against the top right extension plate 11d of the front surface 110c and allows the door 50 to be easily opened. Furthermore, the door 50 can be made to be openable and closeable or unopenable and unclosable simply by rotating the one end of the straight-shaped section of the lever 60a. Still furthermore, with the liquid chromatograph mass spectrometer according to the present invention, since the lever is hidden from view when seen from the front, the appearance is improved.

Other Embodiments (1) The afore-described liquid chromatograph mass spectrometer was configured so that with pin (female part) 62 is fixed to the right side of the front surface 110c. However, the pin (female part) 62 can be configured to be movable in the fore and aft directions.

(2) In the afore-described liquid chromatograph mass spectrometer, extension 60b of the lever 60 was positioned on the right side of the front surface 110c. However, the extension 60b of the lever 60 can be configured so that it is positioned in a recessed section in the shape of a rectangular solid that is formed on the lower right part of the front surface 110e.

POSSIBILITY OF INDUSTRIAL USE

The present invention can be used with mass spectrometers equipped with an ionization chamber.

DESCRIPTION OF NUMERICAL REFERENCES

11: Ionization chamber
14: Mass spectrometer
15: Spray (probe)
19: Solvent removal tube
50, 150: Door
60: Lever
60a: Straight-shaped section
61: Cam (male part)
62: Pin (female part)
110, 210: Chamber (enclosure)
110a, 210a: Upper surface (first side wall)
110b, 210b: Partition (second side wall)
110c, 210c: Front surface (third side wall)

What is claimed is:

1. A mass spectrometer comprising an ionization chamber for ionizing a specimen and a mass spectrometer unit to which ions from said ionization chamber are introduced,
   wherein said ionization chamber comprises:
   an enclosure comprising a first wall surface, a second wall surface and a third wall surface, said enclosure forming an internal space;
   a probe installed on said first wall surface for spraying specimen into said ionization chamber; and
   a tube formed on said second wall surface for connecting the inside of said ionization chamber and the inside of said mass spectrometer unit; and
   wherein a rectangular flat door is disposed on said third wall surface for forming an opening that opens to the inside of said ionization chamber and for closing said opening;
   said door is openable and closeable about a first edge of said rectangular door;
   a lever is formed on a side surface of a second edge of said door that opposes the first edge of said door, said lever comprising a straight-shaped section that is rotatable about a rotation shaft that is perpendicular to said first edge;
   one end of said straight-shaped section of the lever is operated by a person taking measurements, the rotation in a forward direction of the one end of the straight-shaped section of the lever by said person taking measurements causing a male part that is formed on said lever to engage with a female part that is formed on said enclosure and become locked thus making said door unable to be opened and closed and the rotation in a reverse direction of the one end of the straight-shaped section of the lever by said person taking measurements causing the male part that is formed on said lever to disengage from the female part that is formed on said enclosure and becoming unlocked thus allowing said door to be opened and closed; and
   the one end of said straight-shaped section of the lever is rotated in a reverse direction by said person taking measurements to unlock which causes other end of said straight-shaped section of the lever to press against a portion of a third wall surface, creating a force that opens said door.

2. The mass spectrometer according to claim 1 wherein the distance from said one end of said lever to the rotation shaft is longer than the distance from said other end to the rotation shaft.

3. The mass spectrometer according to claim 1 wherein:
   said male part is a columnar structure that is formed on said lever;
   said female part is a columnar structure that is formed on said enclosure;
   said first edge of said rectangular door extends in a vertical direction;
   said door is opened by pulling in the foreground direction; and
   said columnar structure serving as said male part is positioned to the rear of and at the same height as said columnar structure serving as said female part when locked and is not positioned at the same height as said columnar structure serving as said female part when unlocked.

4. The mass spectrometer according to claim 1 further comprising a cover that covers said door and said lever from the front wherein:
   said cover is fixed to said door so that said cover is rotatable about a rotation shaft that is perpendicular to said first edge of said door and is fixed to said one end of said straight-shaped section of the lever; and
   said cover rotates about a rotation shaft that is perpendicular to said first edge of said door together with said lever while covering said door and said lever.

* * * * *